United States Patent [19]

Hoyt et al.

[11] Patent Number: 5,014,913
[45] Date of Patent: May 14, 1991

[54] AIR-FRESHENING DEVICE

[75] Inventors: Earl Hoyt, Franklin Lakes; Manharbhai K. Patel, Saddle Brook, both of N.J.

[73] Assignee: Reckitt & Colman Inc., Wayne, N.J.

[21] Appl. No.: 478,809

[22] Filed: Feb. 12, 1990

[51] Int. Cl.⁵ .............................................. A61L 9/12
[52] U.S. Cl. ...................................... 239/45; 239/57; 239/58
[58] Field of Search ...................... 239/34, 44, 45, 49, 239/51.5, 55, 56, 58, 59, 60

[56] References Cited

U.S. PATENT DOCUMENTS

| 164,481 | 9/1951 | Ellis . | |
|---|---|---|---|
| 181,535 | 11/1957 | Klasky . | |
| 195,324 | 9/1977 | Atkinson . | |
| 2,763,395 | 9/1956 | Meek . | |
| 2,787,496 | 4/1957 | Skaist | 239/45 |
| 2,830,845 | 4/1958 | Cottle . | |
| 2,959,354 | 11/1960 | Beck | 239/55 |
| 3,521,816 | 7/1970 | Wilson | 239/60 |
| 3,698,991 | 10/1972 | Susewitz . | |
| 4,372,490 | 2/1983 | Le Caire, Jr. et al. | 239/59 |
| 4,452,393 | 6/1984 | Schimanski et al. | 239/56 |
| 4,502,630 | 3/1985 | Haworth | 239/34 |
| 4,660,764 | 4/1987 | Joyaux et al. | 239/44 |

Primary Examiner—Andres Kashnikow
Assistant Examiner—Michael J. Forman
Attorney, Agent, or Firm—Frederick H. Rabin

[57] ABSTRACT

An air-freshening device including an air-freshening fluid container having a removable cap with a wick support. A fluid-absorbent medium has an exposed surface on the cap and a wick extends through the cap to the fluid-absorbent medium. An outer closure support for the container has a pair of adjustable closure half-shells. Each half-shell has an internal locking arm for engaging the flange of the cap for controlling the air freshener flow out of the device.

11 Claims, 4 Drawing Sheets

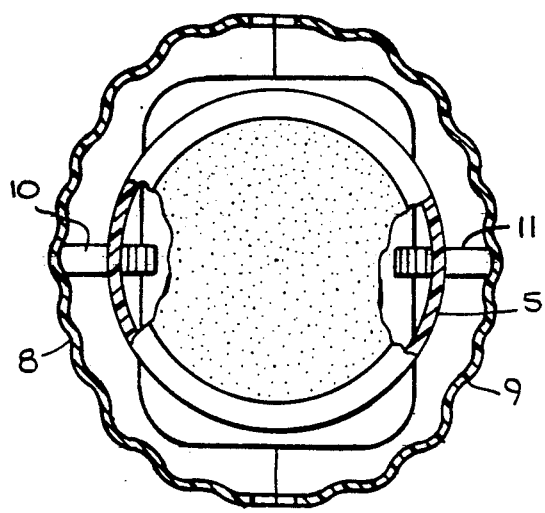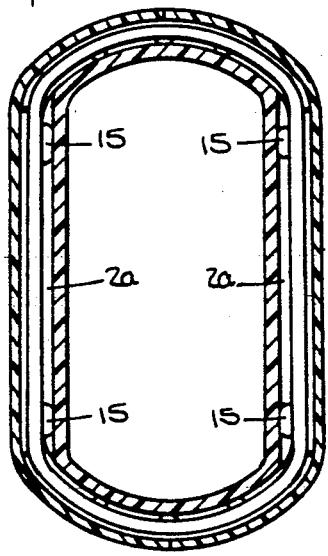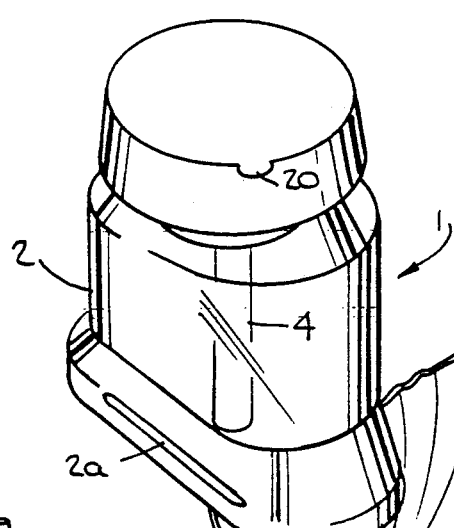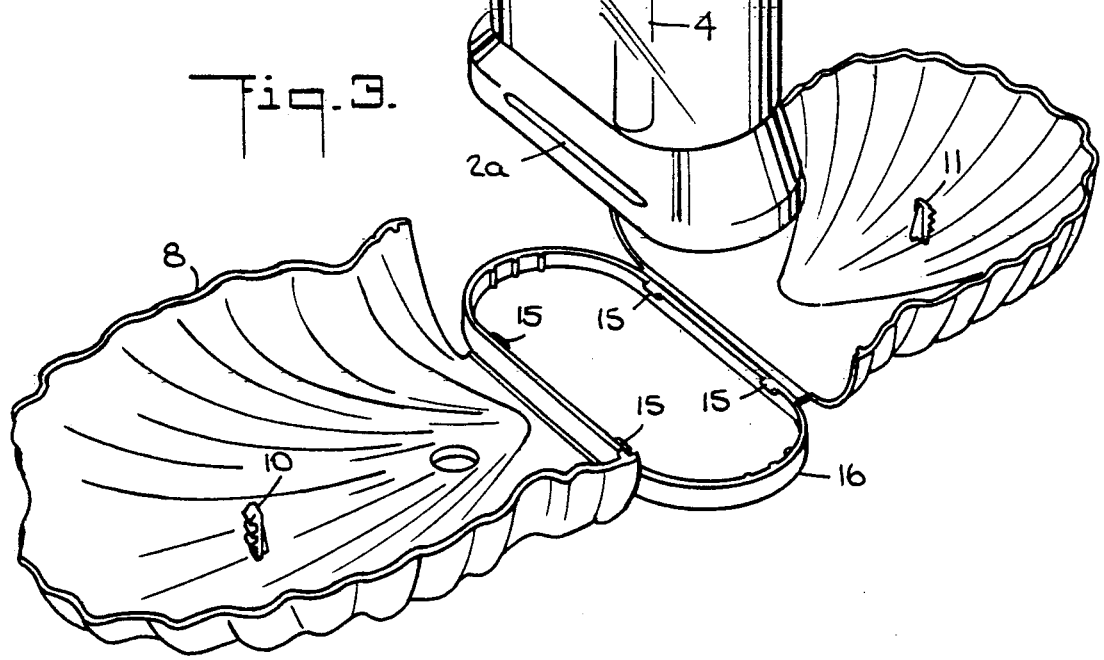

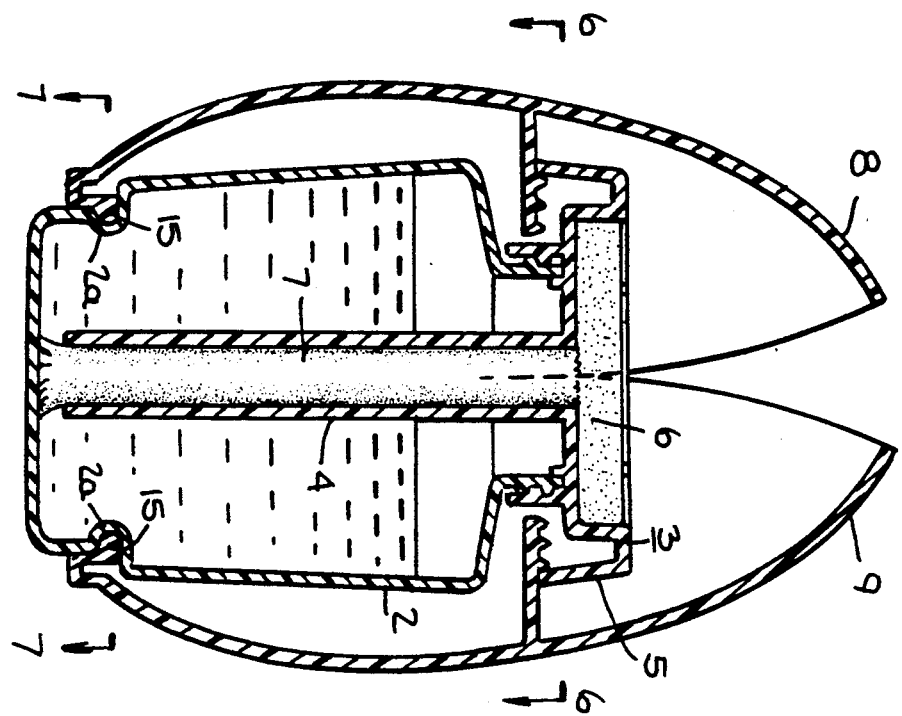
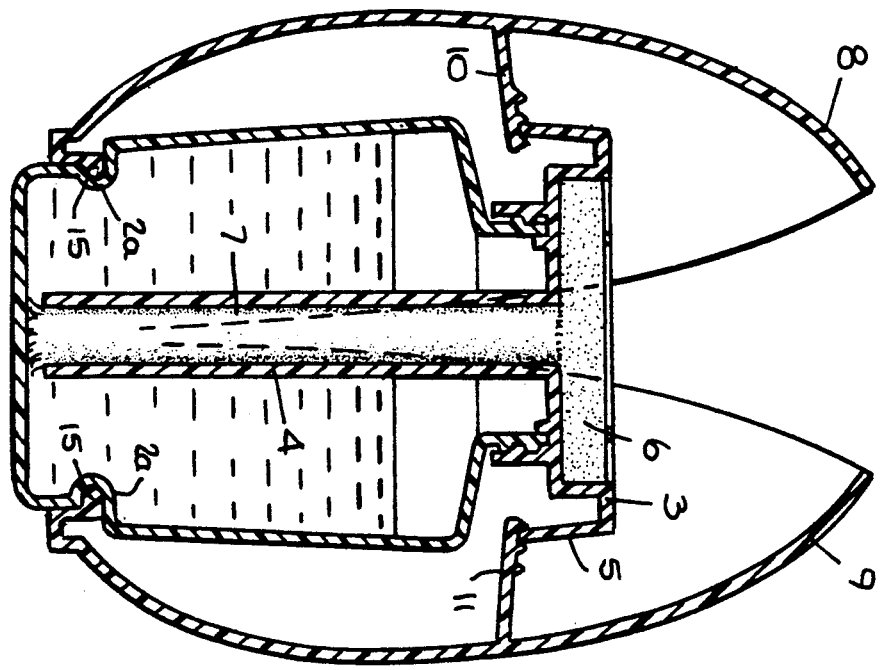

AIR-FRESHENING DEVICE

This invention relates to an air-freshening device, and, more particularly, to an air freshening device capable of providing different values of a controlled flow of air freshener into the environment.

Various fragrance emitting articles are described in the following U.S. Pat. Nos. 195,324-Atkinson, 3,698,991-Susewitz, 2,830,845-Cottle, 2,763,395-Meek, Design patent No. 164,481-Ellis, Design patent No. 181,535-Klasky. In general, these devices are more complex than is desirable or are not capable of emitting controlled and different values of air fragrance flow. A design patent application Ser. No. 473,285 has been filed by on Jan. 26, 1990 directed to the ornamental design of the air-freshening device.

It is an object of the present invention, therefore, to provide a new and improved air-freshening device which avoids one or more of the disadvantages and limitations of prior such devices.

It is another object of the invention to provide a new and improved air-freshening device which is capable of providing different values of controlled air freshener flow to the environment.

In accordance with the invention, an air-freshening device comprises an air-freshening fluid container having a removable cap with a wick support and having a flange. The device includes a fluid-absorbent medium having an exposed surface on the cap. The device also includes a wick extending through the cap to the fluid-absorbent medium. The device also includes an outer closure support for the container having a pair of adjustable closure wings, each wing having an internal locking arm for engaging the flange of the cap.

Also in accordance with the invention, an air-freshening device comprises an air-freshening fluid container having a removable cap with a wick support and having a flange. The device includes a fluid-absorbent medium having an exposed surface on the cap and a wick extending through the cap to the fluid-absorbent medium. The device also includes an outer closure support for the container having a pair of adjustable closure wings. Each wing has an internal locking arm for engaging a portion of the fluid container.

Also in accordance with the invention, an air-freshening device comprises an air-freshening fluid container having a removable cap with a wick support and having a flange. The device includes a fluid-absorbent medium having an exposed surface on the cap. The device also includes a wick extending through the cap to the fluid-absorbent medium. The device also includes an outer closure support for the container having a pair of adjustable closure wings. At least one wing has an internal multi-position locking arm for engaging the other wing.

For a better understanding of the present invention, together with other and further objects thereof, reference is made to the following description, taken in connection with the accompanying drawings, and its scope will be pointed out in the appended claims.

Referring now to the drawings:

FIG. 3 is an exploded perspective view of the air-freshening device in accordance with the invention;

FIG. 4 is a sectional view of the FIG. 1 device in a first position of adjustment;

FIG. 5 is another sectional view of the FIG. 1 device in a different position of adjustment;

FIG. 6 is a sectional view of the FIG. 1 device taken along line 6—6 of FIG. 4;

FIG. 7 is a sectional view of the FIG. 1 device taken along line 7—7 of FIG. 4;

Figure 1:
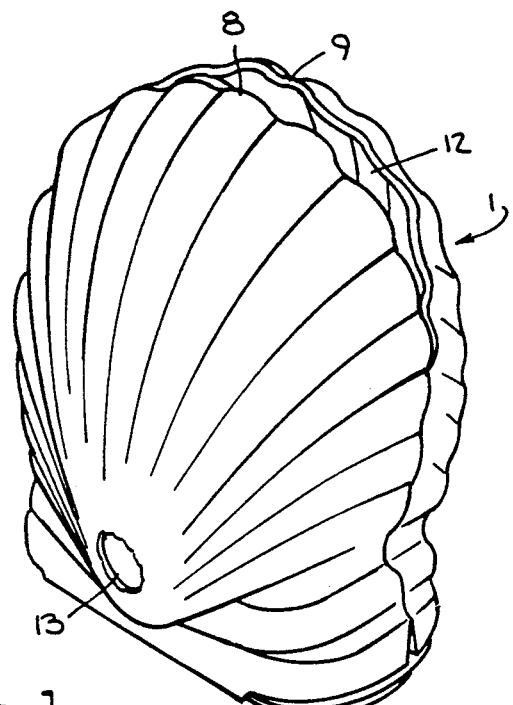
FIG. 1 is a perspective view of an air-freshening device in accordance with the invention.
Figure 2:
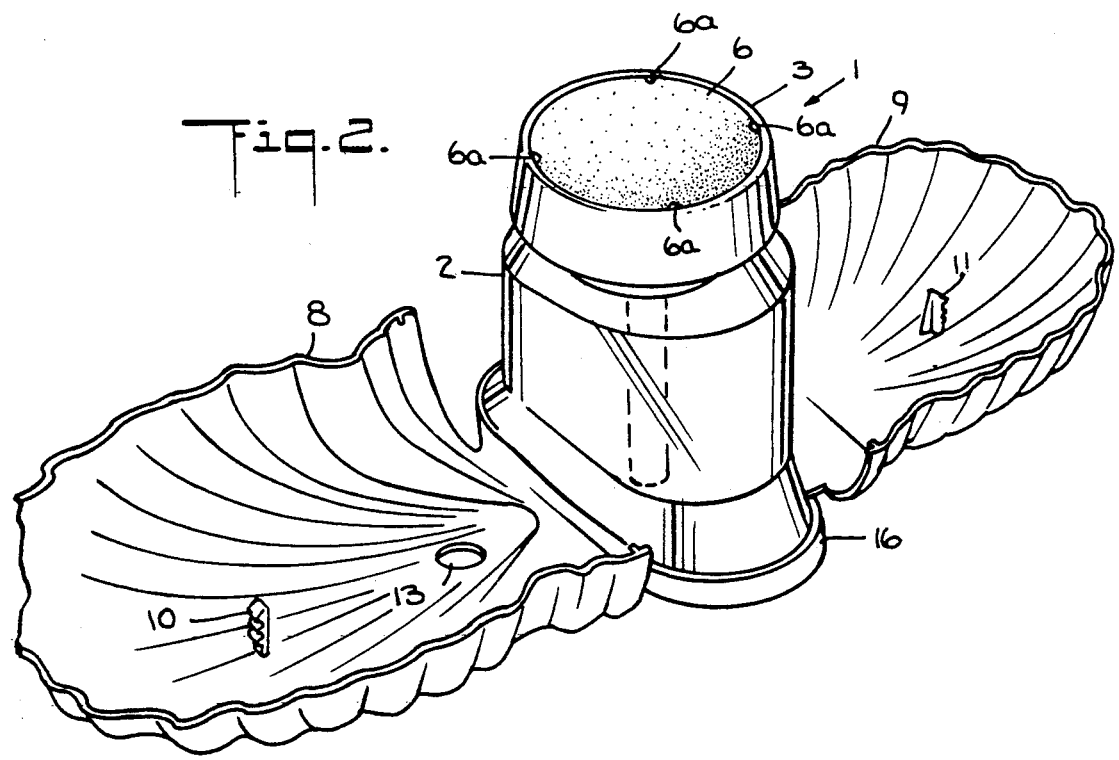
FIG. 2 is a perspective view of an air-freshening device in accordance with the invention in which the wings are entirely open for purposes of illustration only since the device is not intended to be used with the wings in this position.

Referring now more particularly to FIGS. 1, 2 and 3 of the drawings, an air-freshening device 1 comprises an air-freshening fluid container 2 which may, for example, be of transparent plastic. The fluid container has a removable cap 3, for example, of plastic, which screws on the fluid container 2 as represented in FIGS. 4 and 5. The cap 3 has a plastic wick support 4 preferably integral therewith as represented in FIGS. 3, 4 and 5. The cap 3 has a flange 5 represented in FIGS. 4 and 5.

A fluid-absorbent and odor-emitting medium 6 preferably of a suitable porous plastic material with indentations 6a, as represented in FIGS. 2, 4 and 5, is disposed on the cap 3 and has an exposed surface on the cap except as shown in FIG. 3 which includes an air-tight seal 20 on the cap to prevent activation of the device before removal of the seal. The indentations 6a preferably extend the length of the thickness of the medium 6 to allow air flow into the medium 6. A wick 7 preferably of porous plastic material and represented in FIGS. 4 and 5 extends through the cap 3 to contact the fluid-absorbent medium 6.

An outer closure support for the container 2 has a pair of adjustable closure wings 8, 9, as represented in FIGS. 1, 2, 3, 4 and 5. Each wing has an internal locking arm 10, 11, respectively, for engaging the flange 5 of the cap.

The closure wings 8, 9 are maintained in a selected closure relationship as represented in FIG. 4 or FIG. 5 with an opening therebetween determined by engagement of each locking arm 10, 11 with the flange 5 of the cap 3. The locking arms 10, 11 may be symmetrically or asymmetrically engaged with the cap flange 5.

The closure wings 8, 9 are maintained in a selected one of a plurality of closure relationships with a selected one of a plurality of openings therebetween determined by a selected one of a plurality of positions of engagement with each locking arm 10, 11, as represented in FIGS. 4 and 5.

Each locking arm 10, 11 has a plurality of ridges for engaging the flange 5 of the cap 3 at different positions.

Preferably each of the wings 8, 9 is a half-shell which abuts one another in a position of maximum closure represented in FIG. 1 but with an upper escape opening 12 over the cap 3.

FIG. 3 represents in exploded perspective view the fluid container 2 having a base indentation 2a for engaging tabs 15 of a support member 16 to which the half-shells 8, 9 are hinged.

FIG. 6 represents the locking arms 10, 11 in one position of engagement with the flange 5 of the cap 3.

FIG. 7 represents the engagement of the tabs 15 with the indentations 2a.

Considering now the operation of the air-freshening device 1, the cap 3 may be unscrewed from the fluid container and a suitable quantity of liquid air freshener may be poured into the container as represented in FIGS. 4 and 5. The cap 3 may then be utilized to close the container and the arms 10 and 11 of the half-shells 8 and 9 may be closed from the position represented in FIG. 2 to positions such as those represented in FIGS. 4 and 5 to control the volume of the opening over the fluid-absorbent medium on the cap. To activate the device, the impermeable seal represented in FIG. 3 must be removed, preferably before closing the half-shells. The half-shell 8 has an aperture 13 represented in FIGS. 1 and 2 near its bottom to allow viewing into the container enclosed by the half-shells. The half-shell 9 may have a similar aperture if desired. Air freshener is emitted out of the opening 12. By controlling the position of the half-shells 8, 9 by means of the locking arms 10, 11, the volume of the opening 12 and the accompanying air freshening can be suitably controlled.

Figure 8:
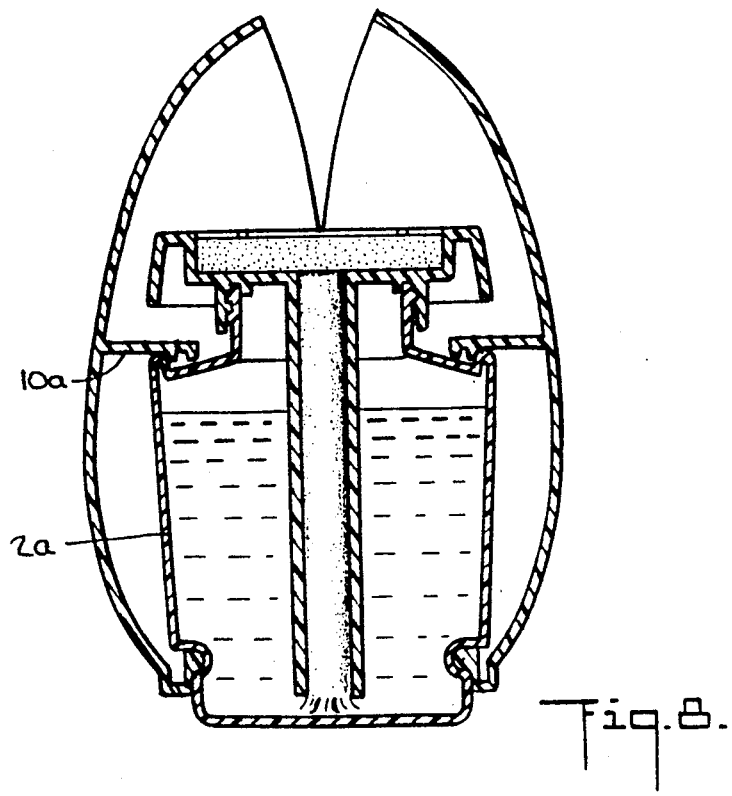
FIG. 8 is a sectional view of another embodiment of the invention.

The FIG. 8 device is similar to the FIG. 1 device except the locking arms 10a, 11a engage a blow-molded ridge of the container 2a instead of engaging the cap of the fluid container.

Figure 9:
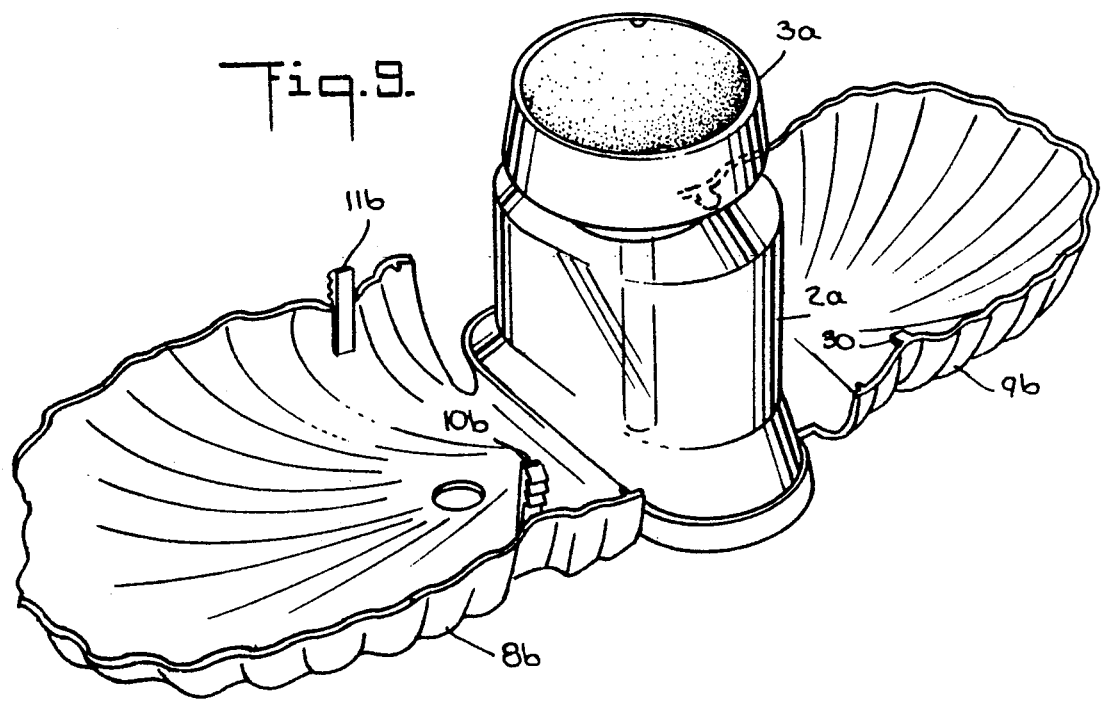
FIG. 9 is a perspective view of another embodiment of the invention.

The FIG. 9 device is similar to the FIG. 1 device except that at least one wing 8b has an internal multi-position locking arm 10b for engaging the other wing 9b. The wing 8b has two locking arms 10b, 11b molded into the wing 8b. These arms snap lock over a small tab, only one of which appears in FIG. 9 as tab 30. There is another such tab hidden from view by the container 2. The shell half 8b locks onto the shall half 9b in an adjustable position. There is no adjustable locking mechanism on the container 2a or the cap 3a.

While there have been described what are at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. An air-freshening device comprising:
   an air-freshening fluid container having a removable cap with a wick support and said cap having a flange;
   a fluid-absorbent medium having an exposed surface on the cap;
   a wick for contacting an air freshening fluid within said container, said wick extending through said cap to said fluid-absorbent medium; and
   an outer closure support for said container having a pair of adjustable closure wings individually having bottoms, each wing having an internal locking arm for engaging said flange of said cap and said support also being attached to said container adjacent said wing bottoms, at least a portion of said closure wings being displaceable from said container and each other and defining a variable opening between said closure wings about said exposed surface for escape of said air freshening fluid.

2. A device in accordance with claim 1 in which said locking arms are sufficiently long to engage said flange with said closure wings displaced from said flange and from each other and said closure wings are maintained in a selected closure relationship with said variable opening therebetween determined by engagement of each locking arm with said flange of said cap.

3. A device in accordance with claim 1 in which said locking arms include means for providing a plurality of closure relationships with said wings and in which said closure wings are maintained in a selected one of said plurality of closure relationships with a selected one of a plurality of said variable openings therebetween determined by a selected one of a plurality of positions of engagement with each locking arm.

4. A device in accordance with claim 1 in which each locking arm has a plurality of ridges for engaging said flange of said cap at different positions.

5. A device in accordance with claim 1 in which each of said wings is a half-shell which abuts one another in a position of maximum closure but with an upper air escape opening over the cap.

6. A device in accordance with claim 1 in which said container is transparent and at least one wing includes an aperture displaced from said cap for viewing into said container.

7. A device in accordance with claim 1 which includes an air-tight impermeable removable seal on said cap over said surface of said fluid-absorbent medium.

8. An air-freshening device comprising:
   an air-freshening fluid container having a removable cap with a wick support and said fluid container having a flange;
   a fluid-absorbent medium having an exposed surface on the cap;
   a contacting an air freshening fluid within said container, said wick extending through said cap to said fluid-absorbent medium; and
   an outer closure support for said container having a pair of adjustable closure wings individually having wing bottoms, each wing having an internal locking arm for engaging said flange of said fluid container and said support also being attached to said container adjacent said wing bottoms, at least a portion of said closure wings being displaceable from said container and each other and defining a variable opening between said closure wings about said exposed surface for escape of said freshening fluid.

9. An air-freshening device in accordance with claim 8, in which each locking arm has a plurality of ridges for engaging said flange of said fluid container at different positions.

10. An air-freshening device comprising:
    an air-freshening fluid container having a removable cap with a wick support and said cap having a flange;
    a fluid-absorbent medium having an exposed surface on the cap;
    a wick for contacting an air freshening fluid within said container, said wick extending through said cap to said fluid absorbent medium; and
    an outer closure support for said container having a pair of adjustable closure wings individually having wing bottoms, at least one wing having an internal multi-position locking arm for engaging another wing and said support also being attached to said container adjacent said wing bottoms, at least a portion of said closure wings being displaceable from said container and each other and defining a variable opening between said closure wings about said exposed surface for escape of said air freshening fluid.

11. A device in accordance with claim 10, in which said at least one locking arm has a plurality of ridges for engaging another wing at different positions.

* * * * *